(12) United States Patent
Nober et al.

(10) Patent No.: US 11,426,530 B2
(45) Date of Patent: Aug. 30, 2022

(54) NEEDLE SHIELD REMOVAL MECHANISM FOR INJECTION DEVICE

(71) Applicant: Sanofi-Aventis Deutschland GMBH, Frankfurt am Main (DE)

(72) Inventors: Peter Nober, Rommersheim (DE); Matthias Rau, Wiesbaden (DE); David Theysen, Mainz (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 170 days.

(21) Appl. No.: 16/466,505

(22) PCT Filed: Dec. 4, 2017

(86) PCT No.: PCT/EP2017/081309
§ 371 (c)(1),
(2) Date: Jun. 4, 2019

(87) PCT Pub. No.: WO2018/104203
PCT Pub. Date: Jun. 14, 2018

(65) Prior Publication Data
US 2019/0336700 A1 Nov. 7, 2019

(30) Foreign Application Priority Data

Dec. 7, 2016 (EP) .................................. 16202659

(51) Int. Cl.
*A61M 5/32* (2006.01)
*A61M 5/20* (2006.01)

(52) U.S. Cl.
CPC ........ *A61M 5/3204* (2013.01); *A61M 5/2033* (2013.01); *A61M 2005/206* (2013.01); *A61M 2005/3267* (2013.01)

(58) Field of Classification Search
CPC .............. A61M 5/3204; A61M 5/2033; A61M 2005/3267; A61M 5/20; A61M 5/3202;
(Continued)

(56) References Cited

U.S. PATENT DOCUMENTS 2,883,984 A * 4/1959 Candido, Jr. ..... A61M 37/0069
604/61
4,150,672 A * 4/1979 Whitney ............. A61M 5/1422
604/246
(Continued)

FOREIGN PATENT DOCUMENTS

CN 101912649 12/2010
CN 102686255 9/2012
(Continued)

OTHER PUBLICATIONS

"Cap, 2011, Houghton Mifflin Harcourt Publishing Company, American Heritage® Dictionary of the English Language, Fifth Edition" (Year: 2011).*
(Continued)

*Primary Examiner* — Nathan R Price
*Assistant Examiner* — Mark A Igel
(74) *Attorney, Agent, or Firm* — Fish & Richardson P.C.

(57) ABSTRACT

An injection device comprises a housing for holding a syringe that has a needle at one end and (ii) a cap that is removably attached to the housing and that has a needle shield to cover said needle. The cap further comprises an actuator and a gear assembly comprising first and second linear gears and a double gear. The gear assembly is configured such that movement of the first linear gear in a first direction rotates the double gear to drive the second linear gear to urge the needle shield away from the housing. The actuator is configured to move the first linear gear in the first direction.

15 Claims, 7 Drawing Sheets

(58) Field of Classification Search
CPC ........ A61M 5/3216; A61M 2005/3217; A61M 2005/3208
See application file for complete search history.

(56) References Cited

U.S. PATENT DOCUMENTS

| | | | |
|---|---|---|---|
| 4,342,311 | A | 8/1982 | Whitney et al. |
| 4,474,572 | A * | 10/1984 | McNaughton .... A61M 37/0069 604/63 |
| 5,328,474 | A | 7/1994 | Raines |
| 2004/0044310 | A1 | 3/2004 | Suzuki |
| 2007/0073224 | A1* | 3/2007 | Dries ................. A61M 5/3243 604/110 |
| 2012/0186075 | A1* | 7/2012 | Edginton ............ A61M 5/2033 29/700 |
| 2016/0184531 | A1* | 6/2016 | Schiller .................. A61M 5/28 604/506 |
| 2017/0080165 | A1* | 3/2017 | Soerensen ........... A61M 5/3202 |
| 2017/0197038 | A1* | 7/2017 | Morlok ................ A61M 5/321 |
| 2018/0353708 | A1* | 12/2018 | Schader .............. A61M 5/2466 |

FOREIGN PATENT DOCUMENTS

| | | | |
|---|---|---|---|
| CN | 102858391 | | 1/2013 |
| CN | 105358195 | | 2/2016 |
| CN | 106102804 | | 11/2016 |
| DE | 102004063652 | | 7/2006 |
| EP | 2468336 | | 6/2012 |
| JP | 2003-093506 | | 4/2003 |
| JP | 2017-508588 | | 3/2017 |
| JP | 2017-516568 | | 6/2017 |
| WO | WO 2003/026725 | | 4/2003 |
| WO | WO 2009/092807 | | 7/2009 |
| WO | WO 2010/127449 | | 11/2010 |
| WO | WO 2011/048223 | | 4/2011 |
| WO | WO 2015/004047 | | 1/2015 |
| WO | WO 2015/110533 | | 7/2015 |
| WO | WO 2015/140262 | | 9/2015 |
| WO | WO-2015140262 | A1 * | 9/2015 .......... A61M 5/2455 |
| WO | WO 2015/185176 | | 12/2015 |

OTHER PUBLICATIONS

PCT International Preliminary Report on Patentability in International Appln. No. PCT/EP2017/081309, dated Jun. 11, 2019, 9 pages.

PCT International Search Report and Written Opinion in International Appln. No. PCT/EP2017/081309, dated Jan. 17, 2018, 11 pages.

* cited by examiner

NEEDLE SHIELD REMOVAL MECHANISM
FOR INJECTION DEVICE

CROSS REFERENCE TO RELATED APPLICATIONS

The present application is the national stage entry of International Patent Application No. PCT/EP2017/081309, filed on Dec. 4, 2017, and claims priority to Application No. EP 16202659.5, filed on Dec. 7, 2016, the disclosures of which are incorporated herein by reference.

TECHNICAL FIELD

The present disclosure relates to an injection device and to a method of removing a cap from a housing of an injection device.

BACKGROUND

Injection devices, such as auto-injectors, are known in the art for dispensing a medicament to the injection site of a patient. Such injection devices typically comprise a body and a cap. A needle syringe is located in the body. The cap is removably attached to the body to shield the needle of the needle syringe. To dispense the medicament, the cap is first removed from the body to expose the needle. The needle is then inserted into the body of the patient at the injection site to dispense the medicament.

It is important that the cap is held onto the body with sufficient force to ensure that the cap is not accidentally removed from the body during transport and storage of the injection device. This ensures that the needle is kept sterile and also prevents the sharp needle from causing injury. However, the force required to hold the cap and body together can make it difficult for the patient to intentionally remove the cap from the body prior to injection, particularly if the patient is elderly or infirm.

SUMMARY

In certain aspects, an improved injection device is provided.

According to some aspects, there is provided an injection device comprising: a housing for holding a syringe that has a needle at one end; a cap that is removably attached to the housing and has a needle shield to cover said needle; a gear assembly comprising first and second linear gears and a double gear, wherein the gear assembly is configured such that movement of the first linear gear in a first direction rotates the double gear to drive the second linear gear to urge the needle shield away from the housing; and, an actuator configured to move the first linear gear in the first direction.

The gear assembly and actuator may be configured to reduce the force that must be exerted by the patient to urge the needle shield away from the body. Therefore, separation of the needle shield from the body can be made easier. In addition, the gear assembly and actuator may allow for a controlled separation of the needle shield from the body. Furthermore, the double gear allows for a compact needle shield removal mechanism that is relatively easy to manufacture and assemble.

In one embodiment, the double gear comprises first and second portions that are fixed relative to each other and share a common rotational axis. In one embodiment, the first portion is configured to engage the first linear gear and the second portion is configured to engage the second linear gear. In one such embodiment, the actuator is configured to be slid by a user to move the first linear gear in the first direction.

The diameters of the first and second portions of the double gear may be the same. In an alternative embodiment, the diameters of the first and second portions are different.

In one embodiment, the gear assembly is configured to have a gear ratio such that a force exerted on the actuator is translated into a larger force being exerted on the needle shield. This reduces the force that must be exerted by the patient to urge the needle shield away from the housing.

In one embodiment, the double gear is rotatably coupled to the housing. In another embodiment, the double gear is rotatably coupled to the cap.

In one embodiment, the actuator is slidable in a longitudinal direction of the housing to urge the needle shield away from the housing. This sliding movement may be easier for the patient to perform and may allow for a more controlled removal of the needle shield from the housing.

In one embodiment, the actuator is located at a distal end of the cap and wherein the actuator is slidable towards a proximal end of the injection device to urge the needle shield away from the housing. Therefore, the patient may press the actuator against a flat surface, such as a table surface, to urge the needle shield away from the housing, This pressing motion simplifies operation of the actuator, particularly if the patient is elderly or infirm.

In another embodiment, the actuator is located at a distal end of the cap and wherein the actuator is slidable away from a proximal end of the injection device to urge the needle shield away from the housing. Therefore, the patient may pull the actuator to urge the needle shield away from the housing. This pulling motion simplifies operation of the actuator, particularly if the patient is elderly or infirm.

In one embodiment, the actuator comprises a space for receiving a finger of a patient.

In one embodiment, the first linear gear and/or second linear gear is configured to engage with the double gear. The first linear gear may be fixed relative to the actuator.

The second linear gear may be fixed relative to the needle shield.

In one embodiment, the first linear gear and/or second linear gear comprises a rack gear.

In one embodiment, one of the second linear gear and the rotary gear is on the housing and the other is on the cap. In an alternative embodiment, said one of the second linear gear and the rotary gear is on a part of the injection device other than the housing, for example, a needle sleeve of the injection device or a part of the syringe. In one embodiment, the injection device comprises a plurality of gear assemblies. This may allow for a more even and balanced exertion of force on the needle shield to urge the needle shield away from the body. For example, if the injection device comprises two gear assemblies then the gear assemblies may be located on opposite sides of the central axis of the injection device to apply a force to the needle shield from both sides of the central axis.

In one embodiment, the needle shield is configured to frictionally engage with said syringe when the cap is attached to the housing.

In one embodiment, the injection device further comprises a syringe having a needle at one end and being received in the housing, wherein the syringe contains a medicament.

In one embodiment, the injection device is an auto-injector.

According to some aspects, there is also provided a method of removing a cap from a housing of an injection device, wherein the housing holds a syringe that has a needle at one end and wherein the cap is removably attached to the housing and has a needle shield to cover the needle, the method comprising: moving an actuator relative to the cap or housing to move a first linear gear in a first direction to rotate a double gear, wherein the injection device comprises a second linear gear that is coupled to the double gear such that said rotation of the double gear drives the second linear gear to urge the needle shield away from the housing.

These and other aspects of the invention will be apparent from and elucidated with reference to the embodiments described hereinafter.

BRIEF DESCRIPTION OF THE FIGURES

Embodiments of the invention will now be described, by way of example only, with reference to the accompanying drawings, in which.

DETAILED DESCRIPTION

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
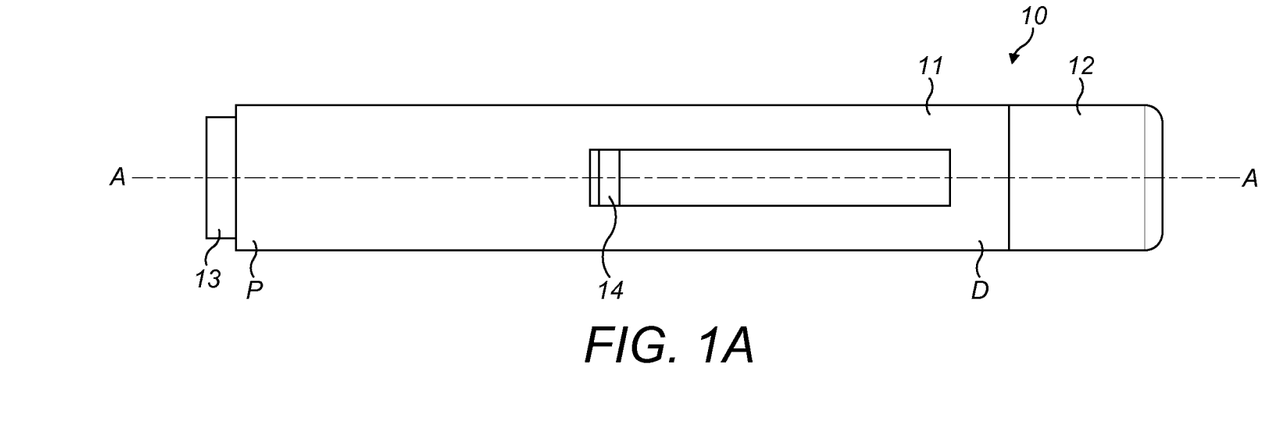
FIG. 1A is a schematic side view of an auto-injector according to some embodiments, with a cap attached to a housing of the auto-injector.
Figure 1B:
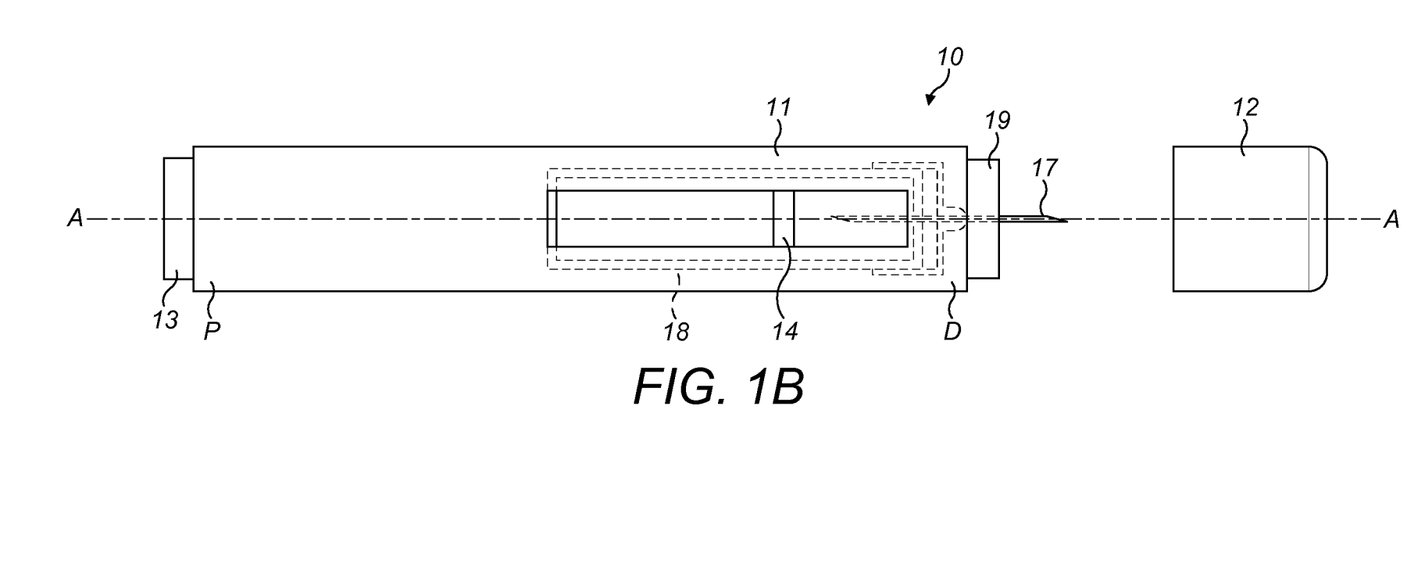
FIG. 1B is a schematic side view of the auto-injector of FIG. 1A, with the cap removed from the housing.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2:
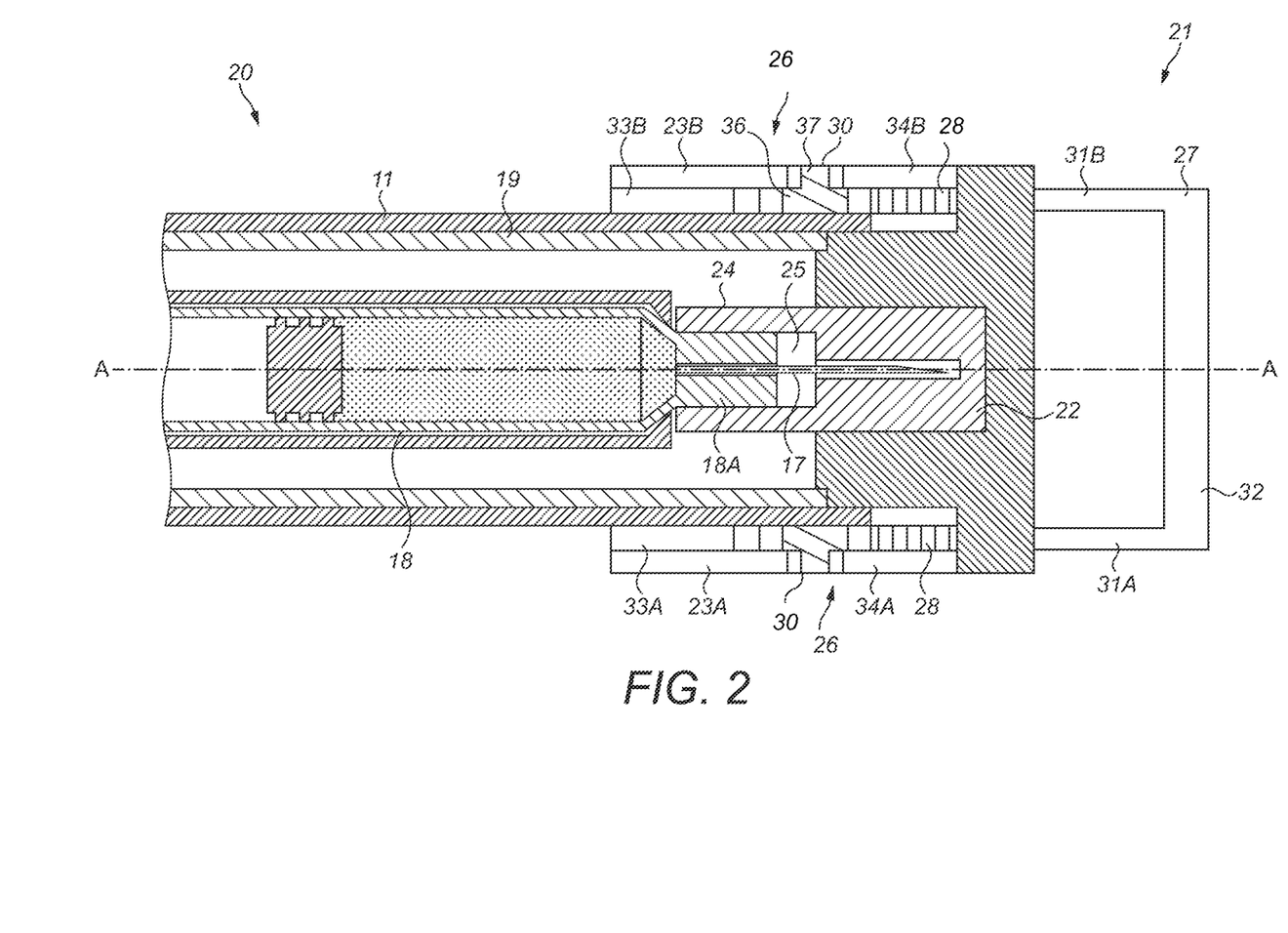
FIG. 2 is a schematic cross-sectional side view of part of an auto-injector according to a first embodiment of the invention, wherein an actuator is in a first position.
Figure 3:
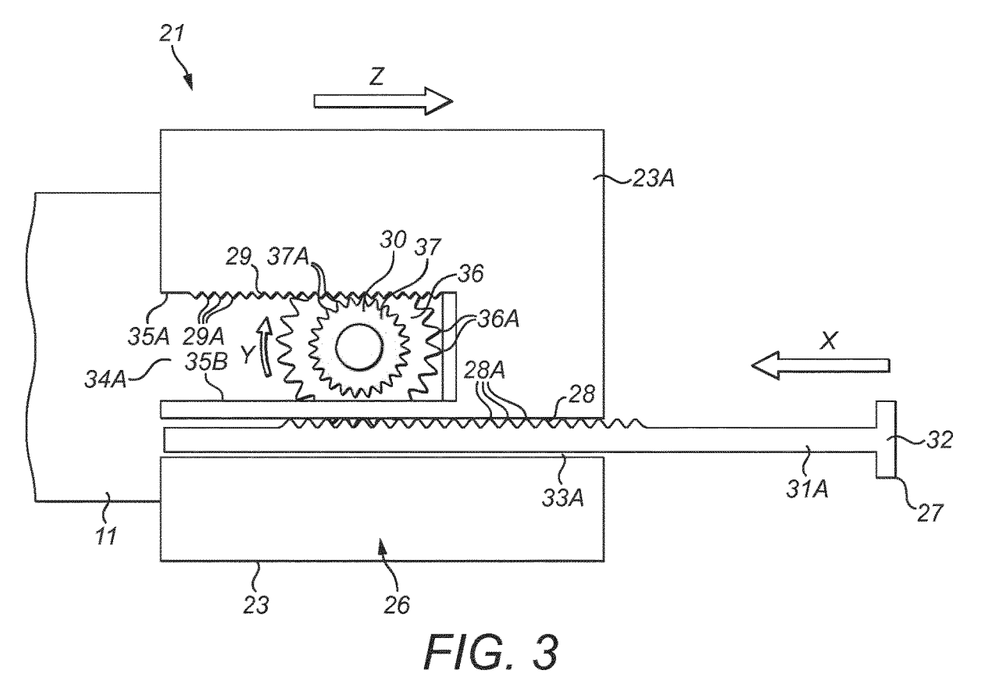
FIG. 3 is a close-up schematic side view of part of the auto-injector of FIG. 2, wherein the actuator is in the first position.
Figure 4:
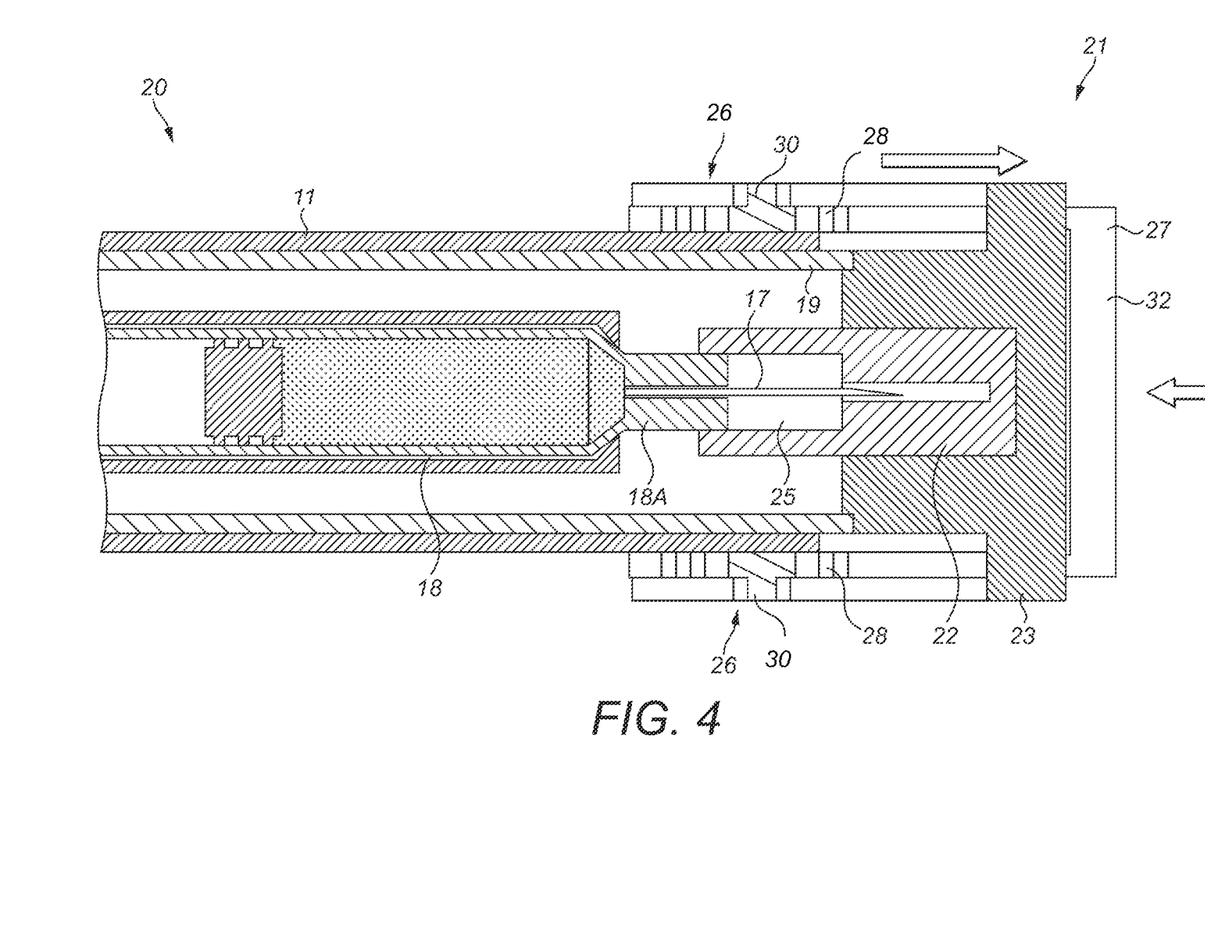
FIG. 4 is a schematic cross-sectional side view of part of the auto-injector of FIG. 2, wherein the actuator is in a second position.

Referring now to FIGS. 2 to 4, an injection device 20 according to a first embodiment of the invention is shown. The injection device 20 is in the form of an auto-injector 20 that has similar features to the auto-injector 10 described above in relation to FIGS. 1A and 1B, with like features retaining the same reference numerals. A difference is that the cap 12 of the auto-injector 10 described above is omitted and is replaced with an alternative cap 21.

The cap 21 of the auto-injector 20 of the first embodiment of the invention comprises a needle shield 22 and an outer cap 23. The needle shield 22 is located inside the outer cap 23 and is fixed thereto. The needle shield 22 comprises a body 24 of impermeable material with a recess 25 in the proximal end of the body 24.

The recess 25 is configured to receive the needle hub 18A and the needle 17 such that the needle 17 is shielded by the body 24. The inside surface of the body 24 and the outside surface of the needle hub 18A frictionally engage to seal the recess 25 to prevent the ingress of air into the recess 25. Thus, the needle 17 is kept sterile when the cap 21 is attached to the housing 11.

The cap 21 further comprises a pair of gear assemblies 26 and an actuator 27. Each gear assembly 26 comprises a first linear gear 28, a second linear gear 29 and a double gear 30. The first and second linear gears 28, 29 of each gear assembly 26 are in the form of rack gears.

The actuator 27 comprises first and second arms 31A, 31B and a connecting member 32 that extends between the distal ends of the first and second arms 31A, 31B. The actuator 27 is generally U-shaped.

The outer cap 23 comprises first and second walls 23A, 23B. The first and second walls 23A, 23B are parallel and integrally formed with a body portion of the outer cap 23. The first and second walls 23A, 23B comprise first and second slots 33A, 33B respectively that extend through the walls 23A, 23B each in a direction parallel to the longitudinal axis A-A of the auto-injector 20. The first and second slots 33A, 33B extend from the distal end to the proximal end of the outer cap 23. The first and second arms 31A, 31B are slidably received in the first and second slots 33A, 33B respectively.

The first and second walls 23A, 23B of outer cap 23 further comprise first and second cut-outs 34A, 34B respectively. The first cut-out 34A extends into the distal end of the first wall 23A towards the proximal end thereof in the direction of the longitudinal axis A-A of the auto-injector 20. The first cut-out 34A is generally rectangular and comprises first and second surfaces 35A, 35B at the edges of the first cut-out 34A which face each other. The first and second surfaces 35A, 35B are parallel. The second cut-out 34B extends into the distal end of the second wall 23B in the direction of the longitudinal axis A-A. The second cut-out 34B is generally rectangular and comprises first and second surfaces (not shown) at the edges of the second cut-out 34B which face each other. The first and second surfaces are parallel.

The first linear gear 28 of each gear assembly 26 is in the form of a plurality of teeth 28A in the surface of a respective one of the first and second arms 31A, 31B. The second linear gear 29 of each gear assembly 26 is in the form of a plurality of teeth 29A in the first surface 35A of a respective one of the first and second cut-outs 34A, 34B.

The double gear 30 of each gear assembly 26 comprises first and second rotary gears 36, 37. The first and second rotary gears 36, 37 are fixed relative to each other and share a common rotational axis. Therefore, rotation of the first rotary gear 36 by a given angular displacement results in corresponding rotation of the second rotary gear 37 in the same direction by an equal angular displacement. The first and second rotary gears 36, 37 may be integrally formed or may be attached to each other, for example, by adhesive. In one embodiment (not shown), the first and second rotary gears are fixedly mounted to one shaft.

Each first rotary gear 36 comprises a plurality of teeth 36A and each second rotary gear 37 comprises a plurality of teeth 37A. The first rotary gear 36 of each gear assembly 26 has a diameter that is larger than the diameter of the second rotary gear 37.

In the present embodiment, the first and second rotary gears 36, 37 of each double gear 30 are spur gears. However, it should be recognised that the first and second rotary gears 36, 37 may instead have a different arrangement, for example, comprising helical or double helical teeth.

The double gears 30 of the pair of gear assemblies 26 are rotatably coupled to the outer surface of the housing 11. The double gears 30 are located on opposite sides of the housing 11. Each double gear 30 is arranged such that the first rotary gear 36 is nearer to the housing 11 than the second rotary gear 37.

Each gear assembly 26 is arranged such that the first linear gear 28 is located on the opposite side of the rotational axis of the double gear 30 to the second linear gear 29. The first linear gear 28 of each double gear 30 faces in the opposite direction to the second linear gear 29.

The first rotary gear 36 of each gear assembly 26 is configured to engage with a respective first linear gear 28. More specifically, the teeth 28A of each first linear gear 28 mesh with the teeth 36A of a respective first rotary gear 36. Therefore, movement of each first linear gear 28 proximally in a linear first direction (shown by arrow 'X' in FIG. 3) results in rotation of the corresponding double gear 30 in a second direction (shown by arrow 'Y' in FIG. 3).

The second rotary gear 37 of each gear assembly 26 is located in a respective cut-out 34A, 34B of the outer cap 23 when the cap 21 is attached to the housing 11. Each second rotary gear 37 is configured to engage with a respective second linear gear 29. More specifically, the teeth 37A of each second rotary gear 37 mesh with the teeth 29A of a respective second linear gear 29. Therefore, rotation of each double gear 30 in the second direction Y results in movement of each second linear gear 29 distally in a linear third direction (shown by arrow 'Z' in FIG. 3).

The actuator 27 is moveable relative to the outer cap 23 from an initial first position (shown in FIGS. 2 and 3) to a second position (shown in FIG. 4). When the actuator 27 is in the first position, the connecting member 32 is spaced from the distal end of the outer cap 23 in the direction of the longitudinal axis A-A of the auto-injector 20. When the actuator 27 is moved to the second position, the actuator 27 is slid proximally relative to the outer cap 23 in the first direction X such that the connecting member 32 moves towards the distal end of the outer cap 23. Movement of the actuator 27 in the first direction X slides the first and second arms 31A, 31B within the respective first and second slots 33A, 33B such that the first linear gears 28 are moved to drive the respective double gears 30 in the second direction Y, thereby urging the second linear gears 29 in the third direction Z.

The cap 21 is initially attached to the housing 11 such that the needle hub 18A is completely received in the recess 25 of the needle shield 22 (as shown in FIG. 2) and the actuator 27 is in the first position. Thus, the needle 17 is covered by the needle shield 22 to keep the needle 17 sterile and to prevent the needle 17 from causing injury to the patient.

To inject medicament, the cap 21 is first removed from the housing 11. Removal of the cap 21 from the housing 11 is achieved by the patient exerting a force on the connecting member 32 of the actuator 27 to urge the actuator 27 to slide relative to the outer cap 23 in the first direction X. This causes each first rotary gear 36 to be driven such that the double gears 30 are rotated relative to the housing 11 in the second direction Y. Rotation of the double gears 30 in the second direction Y causes the second rotary gear 37 of each double gear 30 to drive a respective second linear gear 29 in the third direction Z relative to the housing 11, thereby urging the outer cap 23 and the needle shield 22 axially away from the housing 11.

The needle 17 is fixed relative to the housing 11. Therefore, as the needle shield 22 is urged away from the housing 11 due to the patient moving the actuator 27 in the first direction X, the needle shield 22 moves axially away from the needle 17. The patient continues to move the actuator 27 away from the first position until it reaches the second position (shown in FIG. 4), wherein the majority of the needle hub 18A is no longer received in the recess 25 of the needle shield 22. Once the majority of the needle hub 18A has been removed from the recess 25, the friction between the needle shield 22 and the needle hub 18A is reduced such that the cap 21 can easily be removed from the housing 11 simply by pulling the outer cap 23 distally away from the housing 11 in the third direction Z. In an alternative embodiment (not shown), movement of the actuator 27 to the second position causes the needle shield 22 to move in the third direction Z such that the needle hub 18A is fully removed from the recess 25 in the needle shield 22.

When the cap 21 is initially attached to the housing 11, the outer cap 23 is urged against the needle sleeve 19 to retain the needle sleeve 19 in a retracted position against the force of a biasing member (not shown). In the retracted position, the distal end of the needle sleeve 19 is disposed within the housing 11. When the actuator 27 is moved to the second position, the outer cap 23 moves distally in the third direction Z and thus the needle sleeve 19 is also able to move distally under the force of the biasing member.

When the cap 21 is removed, the biasing member urges the needle sleeve 19 to an extended position, wherein the needle sleeve 19 extends out of the distal end of the housing 11 to shield the needle 17. The distal end of the needle sleeve 19 is then pressed against an injection site of the patient such that the needle sleeve 19 retracts into the housing 11 and the needle 17 enters the injection site. The dispense button (not shown) is then pressed to dispense medicament to the injection site.

The gear assemblies 26 are configured to reduce the force that must be exerted by the patient to remove the needle shield 22 from the needle 17. More specifically, each gear assembly 26 is configured to have a gear ratio such that a first force exerted on the first linear gear 28 by the patient, via the actuator 27, results in a second force, which is larger than the first force, being exerted on the needle shield 22 by the second linear gear 29. Consequently, movement of the actuator 27 relative to the housing 11 in the first direction X by a first distance results in movement of the outer cap 23 relative to the housing 11 in the third direction Z by a second distance that is smaller than the first distance. This reduced gear ratio may be achieved by making the first rotary gear 36 of each double gear 30 larger in diameter than the second rotary gear 37. The gear assemblies 26 therefore makes removal of the cap 21 from the housing 11 easier because the force exerted on the actuator 27 by the patient is translated into a greater force acting on the needle shield 22 to urge the needle shield 22 away from the needle 17. Moreover, the arrangement of the gear assemblies 26 and actuator 27 facilitates a smooth and controlled separation of the needle shield 22 from the needle 17.

In addition, since the actuator 27 is located at the distal end of the outer cap 23 and is moved in a proximal first direction X to remove the needle shield 22, the patient can conveniently urge the needle shield 22 away from the needle 17 by gripping the housing 11 in one hand and pressing the actuator 27 against a horizontal surface, for example, the surface of a table, to drive the first linear gear 28 in the first direction X.

The double gear 30 allows for a compact needle shield removal mechanism. For instance, the first and second linear gears 28, 29 and the first and second rotary gears 36, 37 of the double gear 30 can all be aligned in the longitudinal direction of the injection device 20 to reduce the size of the injection device 20 in the longitudinal direction. Furthermore, only the double gear 30 needs to be rotatably mounted to the injection device 20. The remaining components of the gear assembly 26, namely the first and second linear gears 28, 29, can be fixed relative to the injection device 20, for example, fixed relative to the actuator 27 and needle shield 22. This reduces the complexity of the injection device 20 and therefore simplifies manufacture and assembly.

Figure 5:
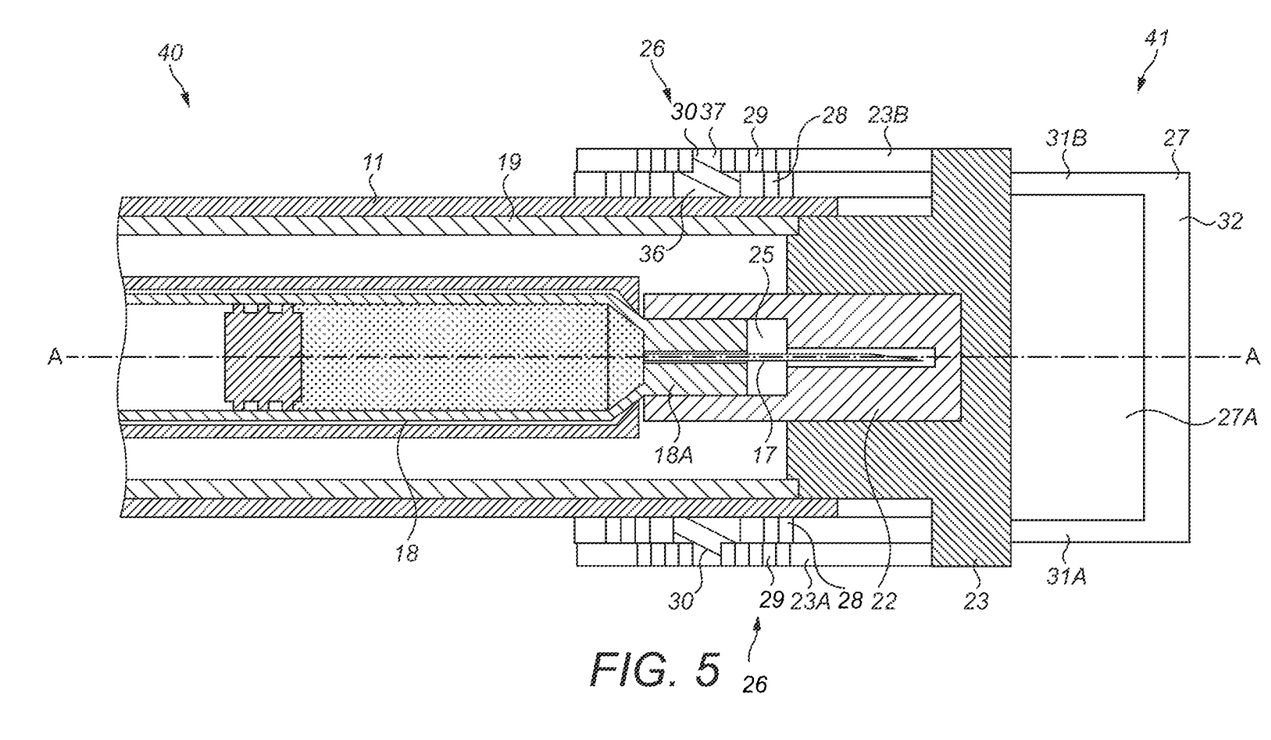
FIG. 5 is a schematic cross-sectional side view of part of an auto-injector according to a second embodiment of the invention, wherein an actuator is in a first position.
Figure 6:
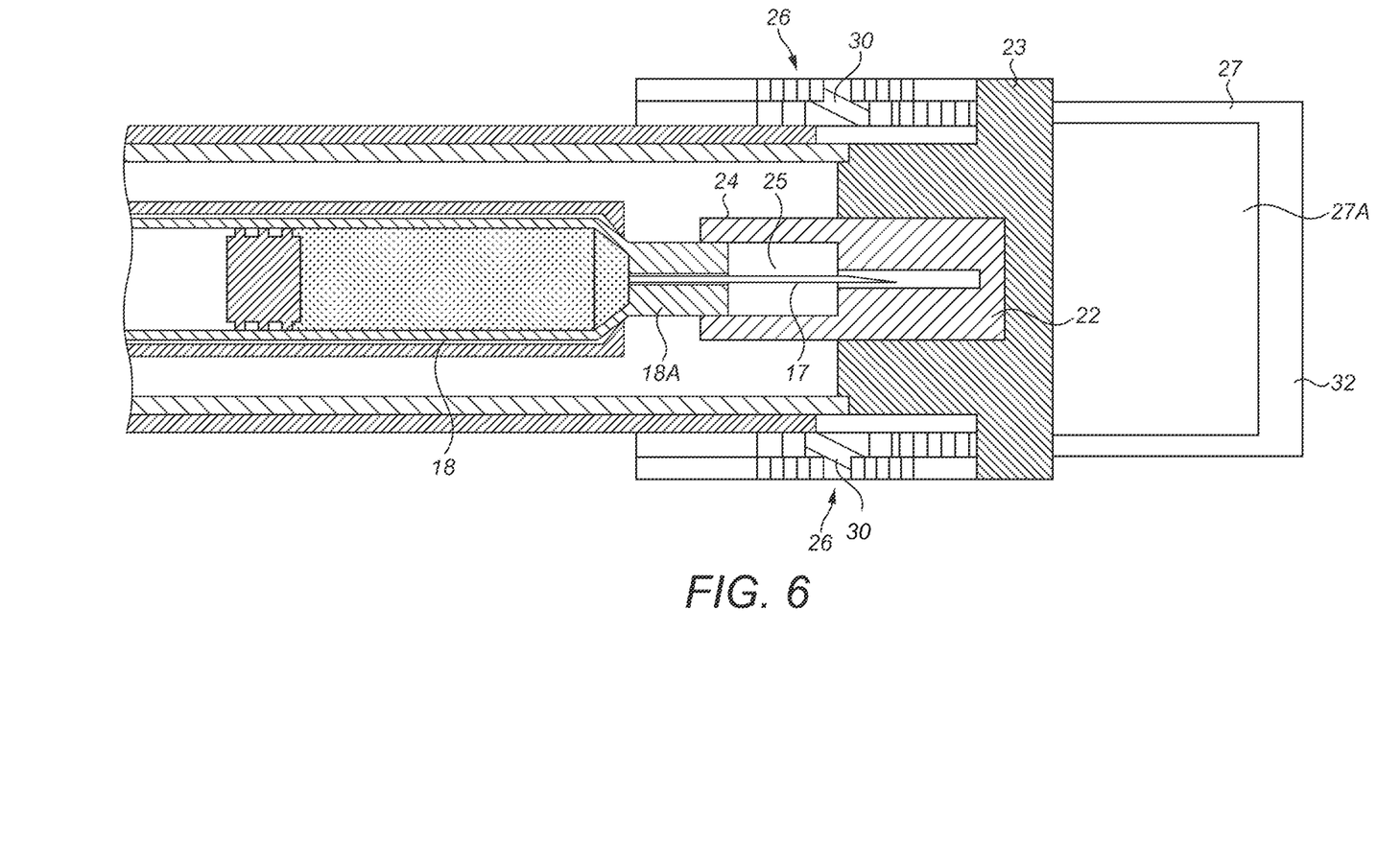
FIG. 6 is a schematic cross-sectional side view of part of the auto-injector of FIG. 5, wherein the actuator is in a second position; and, FIG. 7 is a close-up schematic side view of part of the auto-injector of FIG. 5, wherein the actuator is in the second position.
Figure 7:
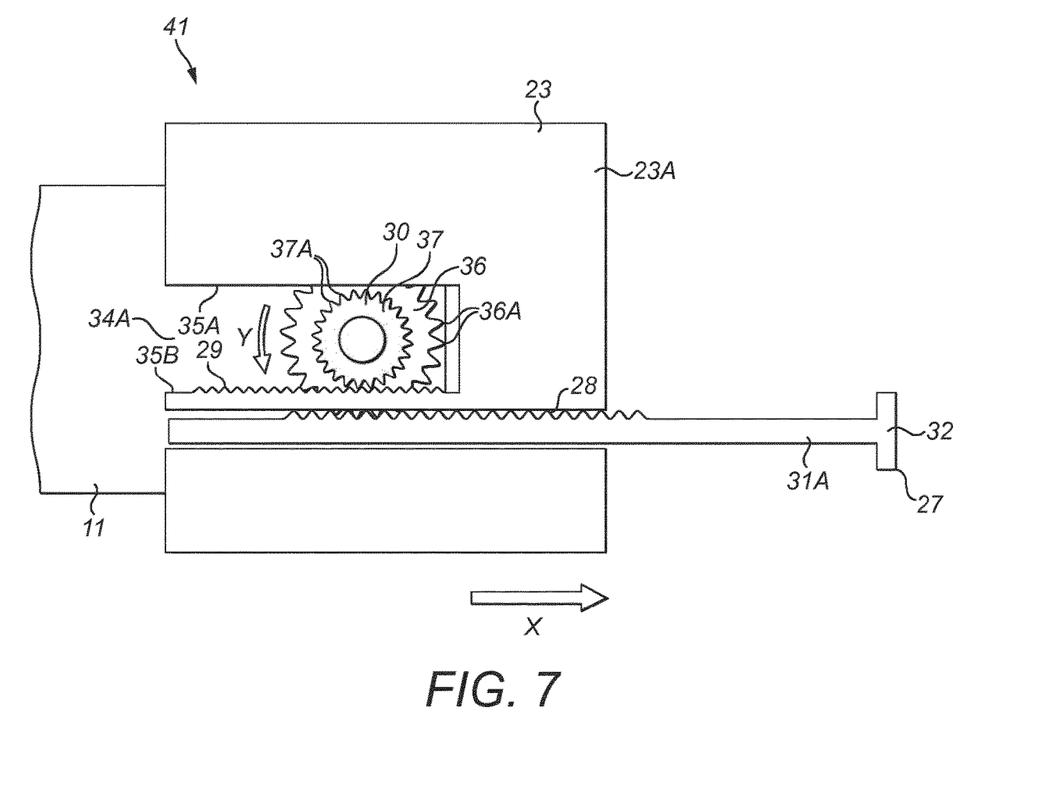

Referring now to FIGS. 5 to 7, part of an injection device 40 according to a second embodiment of the invention is shown. The injection device 40 is in the form of an auto-injector 40 that has similar features to the auto-injector 20 described above in relation to FIGS. 2 to 4, with like features retaining the same reference numerals.

A difference is that the cap 21 of the auto-injector 20 described above is omitted and is replaced with an alternative cap 41 having second linear gears 29 that are formed in the second surface 35B of the respective cut-outs 34A, 34B. Thus, each first linear gear 28 is located on the same side of the rotational axis of the double gear 30 to the respective second linear gear 29. The first and second linear gears 28, 29 thus face in the same direction.

The first rotary gear 36 of each gear assembly 26 is configured to engage with a respective first linear gear 28. More specifically, the teeth 28A of each first linear gear 28 mesh with the teeth 36A of a respective first rotary gear 36. Therefore, movement of each first linear gear 28 distally in a linear first direction (shown by arrow 'X' in FIG. 7) results in rotation of the corresponding double gear 30 in a second direction (shown by arrow 'Y' in FIG. 7).

The second rotary gear 37 of each gear assembly 26 is located in a respective cut-out 34A, 34B of the outer cap 23 when the cap 21 is attached to the housing 11. Each second rotary gear 37 is configured to engage with a respective second linear gear 29. More specifically, the teeth 37A of each second rotary gear 37 mesh with the teeth 29A of a respective second linear gear 29. However, since each second linear gear 29 is formed in the second surface 35B of the respective cut-outs 34A, 34B such that the each second linear gear 29 is located on the same side of the rotational axis of the double gear 30 to the respective first linear gear 28, rotation of each double gear 30 in the second direction Y results in movement of each second linear gear 29 distally in the first direction X.

The actuator 27 is moveable relative to the outer cap 23 from an initial first position (shown in FIG. 5) to a second position (shown in FIGS. 6 and 7). When the actuator 27 is in the first position, the connecting member 32 is spaced from the distal end of the outer cap 23 in the direction of the longitudinal axis A-A of the auto-injector 40 such that the actuator 27 comprises a space 27A located between the connecting member 32 and the outer cap 23. When the actuator 27 is moved to the second position, the actuator 27 is slid distally relative to the outer cap 23 in the first direction X such that the connecting member 32 moves away from the distal end of the outer cap 23. Therefore, the size of the space 27A increases. Movement of the actuator 27 in the first direction X slides the first and second arms 31A, 31B within the respective first and second slots 33A, 33B such that the first linear gears 28 are moved to drive the respective double gears 30 in the second direction Y, thereby urging the second linear gears 29 in the first direction X.

The cap 41 is initially attached to the housing 11 such that the needle hub 18A is completely received in the recess 25 of the needle shield 22 (as shown in FIG. 5) and the actuator 27 is in the first position. Removal of the cap 41 from the housing 11 is achieved by the patient inserting one or more fingers into the space 27A of the actuator 27 and exerting a force on the actuator 27 to pull the actuator 27 distally relative to the housing 11 in the first direction X. This causes each first rotary gear 36 to be driven such that the double gears 30 are rotated relative to the housing 11 in the second direction Y. Rotation of the double gears 30 in the second direction Y causes the second rotary gear 37 of each double gear 30 to drive a respective second linear gear 29 in the first direction X, thereby urging the outer cap 23 and needle shield 22 axially away from the housing 11.

The needle 17 is fixed relative to the housing 11. Therefore, as the needle shield 22 is urged away from the housing 11 due to the patient moving the actuator 27 in the first direction X, the needle shield 22 moves axially away from the needle 17. The patient continues to move the actuator 27 away from the first position until it reaches the second position, wherein the majority of the needle hub 18A is no longer received in the recess 25 of the needle shield 22. Once the majority of the needle hub 18A has been removed from the recess 25 in the needle shield 22, the friction between the needle shield 22 and the needle hub 18A is reduced such that the cap 41 can easily be removed from the housing 11 simply by continuing to pull the actuator 27, and thus the outer cap 23 coupled thereto by the gear assembly 26, away from the housing 11 in the first direction X. In an alternative embodiment (not shown), movement of the actuator 27 to the second position causes the needle shield 22 to move in the first direction X such that the needle hub 18A is fully removed from the recess 25 in the needle shield 22.

As with the first embodiment of the invention, the gear ratio of the gear assemblies 26 reduces the force that must be exerted by the patient to remove the needle shield 22 from the needle 17.

In addition, the pulling motion required to move the actuator 27 from the first position to the second position allows for a smooth and controlled separation of the needle shield 22 from the needle 17.

In the above described embodiments, the auto-injector 20, 40 comprises a pair of gear assemblies 26. However, it should be recognised that the auto-injector 20, 40 may instead comprise a different number of gear assemblies, for example, three or more gear assemblies. In one embodiment (not shown), the auto-injector comprises a single gear assembly. Embodiments having a plurality of gear assemblies have been found to advantageously maintain alignment of the outer cap 23 with the housing 11 when the actuator 27 is moved from the first position to the second position, for example, preventing twisting of the outer cap 23 and thus maintaining alignment of the longitudinal axis of the housing 11 with the longitudinal axis of the outer cap 23.

In the above described embodiments, the gear ratio of the gear assembly 26 is such as to reduce the force that must be exerted by the patient to remove the needle shield 22 from the needle 17. In an alternative embodiment (not shown), the gear ratio of the gear assembly is such that movement of the actuator 27 by a first distance results in movement of the needle shield 22 by a second distance that is greater than the first distance. This may be achieved, for example, by making the diameter of the first rotary gear 36 smaller than the diameter of the second rotary gear 37. In yet another embodiment (not shown), the gear assembly 26 has a gear ratio of 1:1, meaning that movement of the actuator 27 by a first distance results in movement of the needle shield 22 by an equal distance.

In the above described embodiments, each double gear 30 is rotatably coupled to the housing 11 and each second rack gear 29 is fixed relative to the outer cap 23, for example, being formed in the first or second surface 35A, 35B of respective cut-outs 34A, 34B. However, in an alternative embodiment (not shown), each double gear 30 is rotatably coupled to the outer cap 23 and each second linear gear 29 is fixed relative to the housing 11. For example, each second linear gear 29 may comprise a plurality of teeth that are formed in an outer surface of the housing 11 on opposite sides of the longitudinal axis A-A. Alternatively, the second linear gears 29 may comprise rack gears that are fixedly attached to the housing 11.

In the above described embodiments, the actuator 27 is slidably mounted to the outer cap 23. However, in an alternative embodiment (not shown), the actuator 27 is instead slidably mounted to the housing 11.

In the above described embodiments, the first linear gears 28 are integrally formed with the actuator 27 and the second linear gears 29 are integrally formed with the outer cap 23. In alternative embodiments (not shown), the first linear gears 28 are fixedly attached to the actuator 27 and/or the second linear gears 29 are fixedly attached to the outer cap 23. For example, the first linear gears 28 may be adhered to the actuator 27 and/or the second linear gears 29 may be adhered to the outer cap 23.

In the above described embodiments, the actuator 27 is located at the distal end of the outer cap 23. However, in alternative embodiments (not shown), the actuator 27 may be located radially of the outer cap 23. In one such embodiment (not shown), the actuator 27 includes a slider that extends radially from the outer cap 23. The slider may be slid by the patient to move the actuator 27 from the first position to the second position.

In some embodiments, the first and second linear gears and the double gear each comprise a plurality of teeth. However, in alternative embodiments (not shown) the teeth are omitted and instead the first and/or second linear gears frictionally engage with the double gear. In some embodiments the first and second linear gears and/or the double gear comprise a textured surface, for example, having protuberances, recesses or score lines, which increase the friction between the linear gears and double gears. Additionally, or alternatively, the surfaces of the linear gears and/or double gears may be manufactured from a material having a high coefficient of friction, for example, rubber.

In some embodiments, one of the second linear gear and the rotary gear is fixed to the housing and the other is fixed to the cap. In an alternative embodiment (not shown), one of the second linear gear and the rotary gear is fixed to a part of the injection device other than the housing.

For example, said one of the second linear gear and rotary gear may be fixed to the needle sleeve and the other one of the second linear gear and rotary gear may be fixed to the cap. Alternatively, said one of the second linear gear and rotary gear may be fixed to the syringe and the other one of the second linear gear and rotary gear may be fixed to the cap.

In some embodiments, the first linear gear is fixed relative to the actuator. In another embodiment (not shown), the actuator is configured to be moved relative to the first linear gear to move the first linear gear in the first direction. In one embodiment (not shown), the actuator is urged against the first linear gear to move the first linear gear in the first direction. In one embodiment (not shown), the actuator is fixed relative to an intermediate member (not shown), wherein the actuator is moveable to urge the intermediate member against the first linear gear to move the first linear gear in the first direction. The intermediate member may, for example, slide or pivot to be urged against the first linear gear.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers)

and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB -1023, TTP-054, Langlenatide/HM-11260C, CM-3, GLP-1 Eligen, ORMD-0901, NN-9924, NN -9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injection device comprising:
    a housing for holding a syringe that has a needle at one end;
    a cap that is removably attached to the housing and has a needle shield to cover the needle;
    a gear assembly comprising first and second linear gears and a double gear,
    wherein the double gear comprises first and second portions that are fixed relative to each other and share a common rotational axis,
    wherein the first portion is configured to engage the first linear gear and the second portion is configured to engage the second linear gear, and
    wherein the gear assembly is configured such that movement of the first linear gear in a first direction rotates the double gear to drive the second linear gear to urge the needle shield away from the housing to facilitate removal of the needle shield from the needle; and
    an actuator configured to be slid by a user to move the first linear gear in the first direction,
    wherein the actuator is slidable in a longitudinal direction of the housing to urge the needle shield away from the housing, and
    wherein the actuator is located at a distal end of the cap and wherein the actuator is slidable towards a proximal end of the injection device to urge the needle shield away from the housing.

2. The injection device according to claim 1, wherein the gear assembly is configured to have a gear ratio such that a force exerted on the actuator is translated into a larger force being exerted on the needle shield.

3. The injection device according to claim 1, wherein the double gear is rotatably coupled to the housing.

4. The injection device according to claim 1, wherein the double gear is rotatably coupled to the cap.

5. The injection device according to claim 1, wherein the actuator comprises a space for receiving a finger of a patient.

6. The injection device according to claim 1, wherein the first linear gear is fixed relative to the actuator.

7. The injection device according to claim 1, wherein the second linear gear is fixed relative to the needle shield.

8. The injection device according to claim 1, comprising a plurality of gear assemblies.

9. The injection device according to claim 1, wherein the needle shield is configured to frictionally engage with the syringe when the cap is attached to the housing.

10. The injection device according to claim 1, comprising the syringe having the needle at the one end and being received in the housing, wherein the syringe contains a medicament.

11. The injection device of claim 1, wherein a diameter of the first portion of the double gear is different from a diameter of the second portion of the double gear.

12. A needle shield removal mechanism for an injection device, the needle shield removal mechanism comprising:
    a gear assembly comprising first and second linear gears and a double gear,
    wherein the double gear comprises first and second portions that are fixed relative to each other and share a common rotational axis,
    wherein the first portion is configured to engage the first linear gear and the second portion is configured to engage the second linear gear, and
    wherein the gear assembly is configured such that movement of the first linear gear in a first direction rotates the double gear to drive the second linear gear, thereby removing a needle shield from the injection device; and
    an actuator configured to move the first linear gear in the first direction,
    wherein the actuator is slidable in a longitudinal direction of a housing of the injection device to urge the needle shield away from the housing of the injection device, and
    wherein the actuator configured to be located at a distal end of a cap of the injection device and wherein the actuator is slidable towards a proximal end of the injection device to urge the needle shield away from the housing of the injection device.

13. The needle shield removal mechanism according to claim 12, wherein the first linear gear and/or second linear gear is configured to engage with the double gear.

14. The needle shield removal mechanism according to claim 12, wherein the first linear gear is fixed relative to the actuator.

15. A method of removing a cap from a housing of an injection device, the method comprising:
    sliding an actuator located at a distal end of the cap relative to the cap of the injection device or the housing of the injection device in a longitudinal direction of the housing to move a first linear gear in a first direction to rotate a double gear,
    wherein the double gear comprises first and second portions that are fixed relative to each other and share a common rotational axis, and
    wherein the first portion is configured to engage the first linear gear and the second portion is configured to engage a second linear gear that is coupled to the double gear such that rotation of the double gear drives the second linear gear to urge a needle shield of the injection device away from the housing to facilitate removal of the needle shield from a needle of the injection device.

* * * * *

UNITED STATES PATENT AND TRADEMARK OFFICE
CERTIFICATE OF CORRECTION

PATENT NO. : 11,426,530 B2
APPLICATION NO. : 16/466505
DATED : August 30, 2022
INVENTOR(S) : Peter Nober, Matthias Rau and David Theysen It is certified that error appears in the above-identified patent and that said Letters Patent is hereby corrected as shown below:

On the Title Page

Column 2 Item (57) (Abstract), Line 1, after "comprises" insert -- (i) --

Signed and Sealed this
Eighth Day of November, 2022

Katherine Kelly Vidal
*Director of the United States Patent and Trademark Office*